United States Patent [19]
Sangokoya et al.

[11] Patent Number: 5,902,891
[45] Date of Patent: *May 11, 1999

[54] ALUMINOXANE PROCESS AND PRODUCT

[75] Inventors: Samuel A. Sangokoya; Lawrence H. Shepherd, Jr., both of Baton Rouge, La.; Edward A. Burt, Lexington, S.C.

[73] Assignee: Albemarle Corporation, Richmond, Va.

[*] Notice: This patent is subject to a terminal disclaimer.

[21] Appl. No.: 08/980,890

[22] Filed: Dec. 1, 1997

Related U.S. Application Data

[62] Division of application No. 08/556,479, Nov. 13, 1995, Pat. No. 5,693,838.

[51] Int. Cl.$^6$ ....................................................... C07S 5/06
[52] U.S. Cl. ......................... 556/179; 556/181; 556/182; 556/185
[58] Field of Search .................................. 556/179, 181, 556/182, 185

[56] References Cited

U.S. PATENT DOCUMENTS

| | | | |
|---|---|---|---|
| 5,099,050 | 3/1992 | Sangokoya | 556/179 |
| 5,157,137 | 10/1992 | Sangokoya | 556/179 |
| 5,527,930 | 6/1996 | Sangokoya | 556/179 |
| 5,739,368 | 4/1998 | Krzystowczyk et al. | 556/187 |

*Primary Examiner*—Porfirio Nazario-Gonzalez
*Attorney, Agent, or Firm*—Philip M. Pippenger

[57] ABSTRACT

An aluminoxane product is prepared by reacting water which contains a stabilizing agent, such as a lithium halide, with a hydrocarbyl aluminum compound, such as trimethylaluminum, in an organic solvent. The product has increased resistance to gel-formation therein because of the stabilizing agent dissolved in the water used in forming the reaction product.

19 Claims, No Drawings

ALUMINOXANE PROCESS AND PRODUCT

REFERENCE TO RELATED APPLICATION

This application is a division of our prior co-pending application Ser. No. 08/556,479, filed Nov. 13, 1995, now U.S. Pat. No. 5,693,838, issued Dec. 2, 1997.

DESCRIPTION

This invention relates generally to the preparation of aluminoxanes (also known as alumoxanes) and more particularly to the preparation of hydrocarbylaluminoxanes, such as methylaluminoxane, by reacting a hydrocarbyl aluminum compound with water which contains a stabilizing agent, such as a metal salt, which solution is dispersed in an organic solvent.

Vandenberg, U.S. Pat. No. 3,219,591 reported the catalytic activity of compounds formed by the reaction of trialkyl aluminum with limited amounts of water in the polymerization of epichlorohydrin and other oxiranes. Shortly thereafter, Manyik, et al. U.S. Pat. No. 3,242,099 reported the use of aluminoxanes, made by reacting 0.85–1.05 moles of water with hydrocarbyl aluminum compounds such as triisobutylaluminum, as co-catalysts with certain transition metal compounds in the polymerization of mono-unsaturated alpha-olefins; e.g. ethylene and propylene. Isobutylaluminoxane was also made by adding an equal mole quantity of water to a heptane solution of triisobutylaluminum.

Manyik, et al. U.S. Pat. No. 3,300,458 prepared alkylaluminoxane by passing a hydrocarbon through water to form a wet hydrocarbon and mixing the wet hydrocarbon and an alkyl aluminum/hydrocarbon solution in a conduit.

Schoenthal, et al. U.S. Pat. No. 4,730,071 show the preparation of methylaluminoxane by dispersing water in toluene using an ultrasonic bath to cause the dispersion and then adding a toluene solution of trimethylaluminum to the dispersion. Schoenthal, et al. U.S. Pat. No. 4,730,072 is similar except it uses a high speed, high shear-inducing impeller to form the water dispersion.

Edwards, et al. U.S. Pat. No. 4,722,736 describe an aluminoxane process in which water is introduced below the surface of a solution of hydrocarbyl aluminum adjacent to a stirrer which serves to immediately disperse the water in the hydrocarbon solution.

A problem associated with free water addition to trialkylaluminum to produce aluminoxane solutions in organic solvents is that the solutions may produce gel and/or small particles which aggregate to form gel on standing. Even when the particles and/or gel are removed by filtration, additional gel can form in the solution after 2 or 3 weeks, especially when originally-prepared dilute solutions are concentrated to contain higher aluminoxane contents which are convenient for storage, shipment and use.

Sangokoya, U.S. Pat. No. 5,157,137 describes a process for treating MAO with an anhydrous salt and/or hydroxide of an alkali or alkaline earth metal to inhibit gel and gel forming compounds.

We have now discovered a process for making aluminoxanes by free water addition which provides unique, gel free, stable products.

In accordance with this invention there is provided a process for making an aluminoxane, said process comprising reacting water which contains a stabilizing agent with a hydrocarbyl aluminum compound in an organic solvent so as to produce an aluminoxane product.

Also provided is a new stable aluminoxane product prepared by this novel process.

Hydrocarbylaluminoxanes may exist in the form of linear, cyclic, caged or polymeric structures with the simplest compounds being a tetraalkylaluminoxane such as tetramethylaluminoxane, $(CH_3)_2AlOAl(CH_3)_2$, or tetraethylaluminoxane, $(C_2H_5)_2AlOAl(C_2H_5)_2$. The compounds preferred for use in olefin polymerization catalysts usually contain about 4 to 20 of the repeating units:

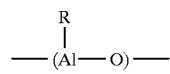

where R is $C_1$–$C_8$ alkyl and is preferably methyl. The exact structure of aluminoxanes has not been defined and they may contain linear, cyclic, caged and/or cross-linked species. Methylaluminoxanes (MAOs) normally have lower solubility in organic solvents than higher alkylaluminoxanes and the methylaluminoxane solutions tend to be cloudy or gelatinous due to the separation of particles and agglomerates. In order to improve the solubility of the methylaluminoxane, higher alkyl groups, e.g. $C_2$ to $C_{20}$, can be included such as by hydrolyzing a mixture of trimethylaluminum with a $C_2$ to $C_{20}$ alkylaluminum compound such as, for example, triethylaluminum, tri-n-propylaluminum, triisobutylaluminum, tri-n-hexylaluminum, tri-n-octylaluminum or a triarylaluminum. Such mixed methyl higher alkyl or aryl aluminoxanes are included in the term "methylaluminoxane" as used herein.

Any hydrocarbyl aluminum compound or mixture of compounds capable of reacting with water to form an aluminoxane can be used. This includes, for example, trialkylaluminum, triarylaluminum, mixed alkyl-aryl aluminum, and the like.

The preferred hydrocarbyl aluminum compounds are the alkyl aluminum compounds, especially trialkylaluminum compounds such as trimethylaluminum, triethylaluminum, triisobutylaluminum, tri-n-hexylaluminum, trioctylaluminum and the like. Of these, the more preferred are the tri-$C_{1-4}$-alkylaluminum compounds.

Of the various hydrocarbyl aluminoxanes, methylaluminoxane and ethylaluminoxane are the more difficult to prepare because of the extreme reactivity of trimethyl aluminum and triethylaluminum with water. The most reactive is trimethylaluminum and, accordingly, the preferred use of the process of the invention is to make methylaluminoxane.

The reaction is carried out in an inert solvent. Any inert solvent can be used. The preferred solvents are aliphatic and aromatic hydrocarbons. Aromatic hydrocarbons are more preferred such as toluene, xylene, ethylbenzene, cumene, mesitylene and the like. The most preferred solvent is toluene.

The concentration of the hydrocarbyl aluminum compounds in the inert solvent can range from about 1–30 weight percent. A preferred concentration is about 5–10 weight percent, more preferably 10–15 weight percent.

The stabilizing agents are combined with the water used to hydrolyze the hydrocarbyl aluminum compounds. The term "stabilizing agent" as used herein includes any water soluble inorganic compound which is effective to provide alkylaluminoxanes having improved solubility in organic solvents when added to the water used to hydrolyze the hydrocarbyl aluminum compound. Preferred are water soluble (at least 1 gram/100 mL $H_2O$ at 25° C.) metal salts and their ammonium analogs and especially alkali and alkaline earth metal halides. Non-limiting examples of such compounds include, NaBr, NaF, NaCl, LiCl, LiBr, LiF, LiI, KCl, MgCl$_2$, MgI$_2$, and the like. Halide salts of other metals as well as ammonium and metal nitrates, nitrites, sulfates, sulfites, phosphates, phosphites, borates, and carbonates can be used, for example Na$_2$SO$_4$, LiBO$_2$, LiCO$_3$, LiNO$_2$, Li$_2$SO$_4$, MgSO$_4$, NaNO$_3$, NaNO$_2$, NaPO$_3$, Na$_2$SO$_3$, Al$_2$(SO$_4$)$_3$Na$_3$PO$_4$, and the like. Hydroxides such as LiOH, Ba(OH)$_2$, KOH, CsOH, NaOH can also be used.

The stabilizing agents are added to make from about 0.05 percent by weight up to saturated solutions in water. Preferably from about 0.1 to 50 percent by weight aqueous solutions of stabilizing agents are used to hydrolyze the hydrocarbyl aluminum compounds.

The stabilizing agent containing aqueous solutions can be combined with the hydrocarbyl aluminum compound in an inert organic solvent by any suitable manner such as the various ways which are known in the art. For example, the process which is described in U.S. Pat. No. 4,908,463 where water dispersed in an organic solvent is mixed with a solution of the hydrocarbyl aluminum in a "T-shaped" reactor. The amount of water dispersed in the solvent is preferably from about 0.25 to 5.0 weight percent, based on the weight of solvent. A more preferred amount is about 0.5 to 3.0 weight percent and most preferred is about 1.0 to 2.5 weight percent. The reactants are combined in proportions to provide from about 0.5 to 4.0 moles of hydrocarbyl aluminum compound per mole of water and from about 5.0 to 10,000 moles of hydrocarbyl aluminum compound per mole of stabilizing agent and, preferably, from about 50 to 5,000 moles of hydrocarbyl aluminum compound per mole of stabilizing agent.

The invention is further illustrated by, but is not intended to be limited to, the following examples.

EXAMPLE 1

An aqueous LiCl solution was prepared which contained 0.35 pounds (158.9 grams) of anhydrous LiCl salt in 3 gallons (11.36 liters) of solution. This salt solution was fed into a flow-through sonicating horn at a rate of 0.15 lbs. (68.1 gms) per hour and emulsified with toluene fed at a rate of 10 pounds (4.54 Kg) per hour. This emulsion was then reacted with a 12 weight percent trimethylaluminum (TMA) in toluene stream fed at a rate of 11 pounds (5.38 Kg) per hour. The TMA-to-water mol ratio was 2.2 to 1. The reaction mixture was then discharged into an eductor, mixed with methylaluminoxane (MAO) product solution from a pump-around loop, and finally discharged into the vapor space of a degassing vessel. The toluene feed to the sonication horn was maintained at a temperature of −2° C. The TMA feed stream was maintained at a temperature of 5° C. The degassing vessel was maintained at a temperature of 20° C.

The crude product was sampled and it was noticed that there was practically no degassing in the sample. This behavior is very different from that observed for samples of crude MAO prepared using plain water. Normally crude MAO will continue to degas for 3 to 4 hours after sampling. The solids formed in the new MAO product also appear to settle faster than the solids in normal MAO crude.

A sample of the new MAO was taken from the product stream during the run and was filtered. The solids produced from the reaction appear to filter easier than those formed by the standard MAO plain-water process. The filtered crude was then batch flashed to concentrate the product. The crude product was concentrated by flashing of the solvent using a 104° C. wall temperature, a 60° C. bulk temperature, and a vacuum of 100 mm Hg. The resulting solution was 8.86 weight percent Al. The TMA content of the solution was 4.84 weight percent TMA. The sample contained less than 20 ppm Cl. The aluminum content equates to a 15 weight percent solution of MAO. This 15 weight percent MAO solution was isolated from the flash pot as a clear liquid.

The increased stability of the new MAO was demonstrated by placing a 15 weight percent solution in an oven at 60° C. for 4 days, along with a 30 weight percent solution of conventional plain-water prepared MAO. After the 4 days the MAO was cloudy, but the new MAO was still clear. The oven temperature was then increased to 65° C. for two more days. The new MAO remained clear. The oven temperature was then raised to 80° C. After one day at 80° C. the new MAO was still clear, but regular MAO was completely gelled.

After the oven test, the 15 weight percent MAO solution was used in a polymerization test to determine if it was active as a co-catalyst. Three mL of the 15 weight percent MAO solution were added to 100 mL of toluene. To this solution, 0.25 mL of a solution of 18 mg of zirconocene dichloride—(C$_5$H$_5$)$_2$ZrCl$_2$—dissolved in 18 mL toluene was added. The solution was stirred and heated in an oil bath to 80° C. A constant pressure of ethylene (60 psig) gas was then placed on the reaction vessel. After 35 minutes, the vessel was removed from the oil bath and the pressure was released. The polyethylene product was collected by filtration, washed and dried. The final yield was 7.05 grams of polyethylene.

The polymerization test was repeated with standard plain-water prepared MAO. A change was made in the volume of MAO solution added based on the calculated weight percent MAO. Two mL of 23 weight percent MAO was added to 100 mL of toluene and then 0.25 mL of the zirconcene dichloride toluene solution was added. The reaction was performed under the same conditions for the same length of time as the above polymerization test. The polyethylene was collected, washed and dried. The final yield was 7.88 grams. Allowing for experimental error, this result equates to approximately the same degree of reactivity as the new MAO which has been heat aged. This demonstrates that the improved stability of the MAO prepared in accordance with the process of the invention is achieved without loss of activity.

EXAMPLE 2

MAO was prepared using the same LiCl salt solution as in Example 1, but the feed rates and temperatures were somewhat different.

The salt solution was fed at a rate of 0.16 lbs (72.6 gms)/hr. The toluene stream was fed at 11.6 lbs (5.26 Kg)/hr. The TMA stream was fed at 11.6 lbs (5.26 Kg)/hr. These feed rates produced a TMA-to-water mole ratio of 2.22 to 1. The temperature of degassing vessel for the second run was maintained at 10° C. The other feed temperatures were maintained the same as in Example 1.

A sample of the MAO was taken from the second run and was filtered and flashed under the same conditions as the first run sample of Example 1. The final weight percent Al of this sample was 11.4. The sample contained 7.96 weight percent TMA and 0.01 weight percent Cl. These results equate to an 18 weight percent MAO solution. This solution was clear upon leaving the flash pot. A portion of the sample was placed in an oven at 65° C. for two days and it remained clear and gel free. The oven was then increased to 80° C., and a sample of standard 10 weight percent MAO was placed in the oven. After one day the new MAO was still clear, but the 10 weight percent MAO began turning cloudy.

The solids filtered from the sample from Example 2 were analyzed. The solids contained 11.5 weight percent Al, no detectable TMA, 0.35 weight percent Cl, and a gas/Al mole ratio of 1.47. This ratio is approximately equivalent to that of standard plain-water prepared MAO. These results indicate that these solids could be a higher molecular weight MAO. An experiment was conducted to determine if the solids could be used as both an activator and a support for a metallocene catalyst. The solid was rinsed from the bottle with toluene and collected on a coarse frit. The solids were then washed with isopentane and a fine white powder resulted. The solid was removed from the frit and slurried with toluene. Six mL of a 0.100 gram of zirconocene dichloride dissolved in 60 mL toluene solution was then added to the slurry and the resulting mixture agitated. The slurry began changing color from white to peach colored. After approximately one-half hour, the slurry was transferred to the coarse frit for filtering. The toluene was filtered from the solid. The peach-colored solid was then rinsed with isopentane. Upon rinsing, the solid turned to a white powder. One-half gram of this solid was placed into a reaction vessel and 25 mL of toluene was added to produce a slurry. The vessel was then placed in an oil bath at 80° C. and the slurry was stirred at this temperature. Ethylene was applied to the vessel at a continuous pressure of 60 psig while being maintained at 80° C. After 10 minutes, the vessel was removed from the oil bath and the pressure on the vessel was released. The polyethylene produced from this reaction was washed, filtered, and dried. The final yield of polyethylene was 2.1 grams.

What is claimed is as follows:

1. An aluminoxane comprising the reaction product of (A) free, liquid water which has a stabilizing agent dissolved therein, and (B) a hydrocarbyl aluminum compound, said reaction product having increased resistance to gel-formation therein because of the stabilizing agent dissolved in the free, liquid water used in forming said reaction product.

2. The product of claim 1 wherein the stabilizing agent dissolved in the free, liquid water is selected from the group consisting of metal salts and their ammonium analogs, including mixtures thereof.

3. The product of claim 1 wherein the stabilizing agent dissolved in the free, liquid water is at least one alkali metal salt or at least one alkaline earth metal salt.

4. The product of claim 1 wherein the stabilizing agent dissolved in the free, liquid water is a lithium halide.

5. The product of claim 1 wherein the hydrocarbyl aluminum compound is a trialkylaluminum.

6. The product of claim 5 wherein the stabilizing agent dissolved in the free, liquid water is selected from the group consisting of metal salts and their ammonium analogs, including mixtures thereof.

7. The product of claim 5 wherein the stabilizing agent dissolved in the free, liquid water is at least one alkali metal salt or at least one alkaline earth metal salt.

8. The product of claim 5 wherein the stabilizing agent dissolved in the free, liquid water is a lithium halide.

9. The product of claim 5 wherein the trialkylaluminum is trimethylaluminum.

10. The product of claim 9 wherein the stabilizing agent dissolved in the free, liquid water is selected from the group consisting of metal salts and their ammonium analogs, including mixtures thereof.

11. The product of claim 9 wherein the stabilizing agent dissolved in the free, liquid water is at least one alkali metal salt or at least one alkaline earth metal salt.

12. The product of claim 9 wherein the stabilizing agent dissolved in the free, liquid water is a lithium halide.

13. The product of claim 9 wherein the stabilizing agent dissolved in the free, liquid water is lithium chloride.

14. The product of any of claims 1–13 wherein the product is dissolved in an organic solvent.

15. A solution in an organic solvent of an aluminoxane comprising the reaction product of (A) free, liquid water which has an aluminoxane gelation inhibitor dissolved therein, and (B) a hydrocarbyl aluminum compound, said solution being characterized by remaining clear and gel-free longer than an identical solution made and stored in the same way except made without said aluminoxane gelation inhibitor.

16. A solution of claim 15 wherein the aluminoxane is a methylaluminoxane and wherein the organic solvent is a hydrocarbon solvent.

17. A solution of claim 16 wherein the aluminoxane gelation inhibitor dissolved in the free, liquid water is a lithium halide.

18. A solution of claim 16 wherein the aluminoxane gelation inhibitor dissolved in the free, liquid water is lithium chloride.

19. A solution of any of claims 15–18 wherein said reaction product is formed in situ in said organic solvent.

* * * * *